United States Patent
Suda et al.

(10) Patent No.: US 8,944,995 B2
(45) Date of Patent: Feb. 3, 2015

(54) INSERTION DEVICE AND ENDOSCOPE

(75) Inventors: Shinichirou Suda, Sendai (JP); Yoichi Haga, Sendai (JP); Tadao Matsunaga, Sendai (JP)

(73) Assignee: Tohoku University, Sendai-shi (JP)

( * ) Notice: Subject to any disclaimer, the term of this patent is extended or adjusted under 35 U.S.C. 154(b) by 85 days.

(21) Appl. No.: 13/510,806

(22) PCT Filed: Nov. 22, 2010

(86) PCT No.: PCT/JP2010/070828
§ 371 (c)(1),
(2), (4) Date: May 18, 2012

(87) PCT Pub. No.: WO2011/062287
PCT Pub. Date: May 26, 2011

(65) Prior Publication Data
US 2012/0232346 A1    Sep. 13, 2012

(30) Foreign Application Priority Data
Nov. 20, 2009 (JP) ................... 2009-265541

(51) Int. Cl.
*A61B 1/00* (2006.01)
*A61B 1/05* (2006.01)
(Continued)

(52) U.S. Cl.
CPC ............. *A61B 1/05* (2013.01); *A61B 1/0008* (2013.01); *A61B 1/00181* (2013.01);
(Continued)

(58) Field of Classification Search
USPC ............. 600/106, 142, 146, 151, 164–165, 600/170–173
See application file for complete search history.

(56) References Cited

U.S. PATENT DOCUMENTS 5,166,787 A * 11/1992 Irion ....................... 348/75
5,381,784 A    1/1995 Adair
(Continued)

FOREIGN PATENT DOCUMENTS

| JP | A-59-228620 | 12/1984 |
| JP | A-4-500768  | 2/1992  |

(Continued)

OTHER PUBLICATIONS

Tadashi Morokuma, *Naishikyo Tekunoroji* (Endoscope Technology), Shokabo, pp. 24 and 26 (1999), with abstract.
(Continued)

*Primary Examiner* — Matthew J Kasztejna
(74) *Attorney, Agent, or Firm* — Oliff PLC

(57) ABSTRACT

An insertion device and an endoscope which are inserted and extracted through a small incision and have multiple functions. A device body has grip forceps as a treatment means. A first folding back section and a second folding back section are provided at a distal portion of the device body such that the first and second folding back sections are aligned in a row in the longitudinal direction of the device body. The first folding back section and the second folding back section respectively have image obtaining means. An operation means can move the first folding back section to a folded back position in which the first folding back section is folded back relative to the second folding back section, and can also move the second folding back section to a position in which the second folding back section is folded back relative to the device body.

16 Claims, 5 Drawing Sheets

(51) Int. Cl.
*A61B 1/012* (2006.01)
*A61B 1/018* (2006.01)
*A61B 1/313* (2006.01)
A61B 17/34 (2006.01)
A61M 25/00 (2006.01)
A61M 25/01 (2006.01)
A61B 17/00 (2006.01)

(52) U.S. Cl.
CPC .............. *A61B 1/0125* (2013.01); *A61B 1/018* (2013.01); *A61B 1/313* (2013.01); *A61B 2017/3443* (2013.01); *A61M 25/0074* (2013.01); *A61M 25/0133* (2013.01); *A61B 2017/003* (2013.01)
USPC ........... 600/106; 600/129; 600/142; 600/146; 600/151; 600/164; 600/165; 600/170; 600/171

(56) References Cited

U.S. PATENT DOCUMENTS

| | | | |
|---|---|---|---|
| 5,782,752 A | 7/1998 | Lichtman et al. | |
| 5,895,350 A * | 4/1999 | Hori | 600/167 |
| 7,322,934 B2 * | 1/2008 | Miyake et al. | 600/173 |
| 7,621,869 B2 * | 11/2009 | Ratnakar | 600/173 |
| 8,277,373 B2 * | 10/2012 | Maahs et al. | 600/107 |
| 8,289,381 B2 * | 10/2012 | Bayer et al. | 348/65 |
| 2003/0120130 A1 | 6/2003 | Glukhovsky et al. | |
| 2005/0038317 A1 * | 2/2005 | Ratnakar | 600/101 |
| 2005/0234294 A1 | 10/2005 | Saadat et al. | |
| 2006/0252994 A1 * | 11/2006 | Ratnakar | 600/173 |
| 2008/0051629 A1 | 2/2008 | Sugiyama et al. | |
| 2009/0023998 A1 * | 1/2009 | Ratnakar | 600/121 |
| 2010/0217076 A1 * | 8/2010 | Ratnakar | 600/104 |

FOREIGN PATENT DOCUMENTS

| | | |
|---|---|---|
| JP | A-8-101351 | 4/1996 |
| JP | A-9-266879 | 10/1997 |
| JP | A-11-506973 | 6/1999 |
| JP | A-2003-220023 | 8/2003 |
| JP | A-2005-46361 | 2/2005 |
| JP | A-2007-236753 | 9/2007 |
| JP | A-2007-532240 | 11/2007 |
| WO | WO 91/00049 | 1/1991 |
| WO | WO 97/37583 | 10/1997 |
| WO | WO 2005/104927 A2 | 11/2005 |

OTHER PUBLICATIONS

Inst. of Biomedical Engineering, Tokyo Women'S Medical Coll., 21 *seiki wo kirihiraku sentan iryo: baiomedicaru/enjiniaringu nyumon* (Advanced Medicine for Leading the 21$^{st}$ Century—An Introduction to Biomedical Engineering), Newton Press, p. 34 (1999), with abstract.

Norihito Wada et al., *R-scope wo mochiita i-ESD* (Gastric ESD using R-scope), Shokakinaishikyou, vol. 19, No. 5, pp. 657-661 (2007).

Mar. 5, 2012 International Preliminary Report on Patentability issued in International Patent Application No. PCT/JP2010/070828 (with translation).

* cited by examiner

INSERTION DEVICE AND ENDOSCOPE

TECHNICAL FIELD

The present invention relates to an insertion device and an endoscope for medical or industrial use.

BACKGROUND ART

Recently, as a replacement for conventional laparotomy surgeries, endoscopic surgeries such as a laparoscopic surgery are performed. An endoscopic surgery is performed by making a small incision in the body surface and inserting therein a minimally-invasive insertion device such as a rigid endoscope, forceps and an incision tool of narrow diameters, and its effect is comparable to that of a laparotomy surgery. In endoscopic surgeries, the incisions can be made relatively smaller than those in laparotomy surgeries, thus reducing physical and mental burden of the patient.

On the other hand, as conventional insertion devices, there is a flexible endoscope that has a configuration in which the tip of the insertion section can be bent (for example, see Patent Literature 1 or 2 and Non-Patent Literature 1) and a rigid endoscope having a rigid, rod-like insertion section. Also, there is a multifunctional endoscope comprising one endoscope equipped with a plurality of means including an observation means such as a CCD camera and a treatment means such as grip forceps or a snare (for example, see Non-Patent Literature 2 or 3).

CITATION LIST

Patent Literature

Patent Literature 1: Japanese Unexamined Patent Application Publication No. S59-228620
Patent Literature 2: Japanese Unexamined Patent Application Publication No. 2007-236753

Non-Patent Literature

Non-Patent Literature 1: Tadashi MOROKUMA, *Naishikyo Tekunoroji* (Endoscope Technology), Shokabo, pp. 24 and 26 (1999).
Non-Patent Literature 2: Inst. of Biomedical Engineering, Tokyo Women's Medical Coll, 21-*seiki wo kirihiraku sentan iryo: baiomedikaru/enjiniaringu nyumon* (Advanced Medicine for Leading the 21$^{st}$ Century—An Introduction to Biomedical Engineering), Newton Press, p.34 (1999).
Non-Patent Literature 3: Norihito WADA, et al., *R-scope wo mochiita i-ESD* (Gastric ESD using R-scope), Shokaki-naishikyou, Vol. 19, No. 5, pp. 657-661 (2007).

SUMMARY OF INVENTION

Technical Problem

However, a multifunctional endoscope that is a conventional insertion device was problematic in that if more functions are added, the external diameter of the endoscope becomes larger, and consequently, when used in an endoscopic surgery such as a laparoscopic surgery, it caused the incision to be larger and increased the burden of the patient. Furthermore, it was problematic in that if the incision was kept small, the functions mounted on the endoscope were limited. In the case of an insertion device for industrial use, it was also problematic in that if the insertion opening was small, the functions mounted were limited.

The present invention was created with respect to such problems and an object thereof is to provide an insertion device and an endoscope which are readily inserted and extracted through a small incision and have multiple functions.

Technical Solution

To achieve the above object, the insertion device according to the present invention comprises: an elongated device body having at least one of various means including an observation means, a diagnosis means and a treatment means; a folding back section having at least one of the various means and provided at a distal portion of the device body in such a manner that the folding back section can be folded back to a proximal side of the device body; and an operation means provided in such a manner that the operation means can move the folding back section to a serially located position in which the folding back section is aligned with the distal portion of the device body and to a folded back position in which the folding back section is folded back to the proximal side of the device body; wherein when the folding back section is moved to the folded back position by the operation means, the means of the device body functions in a distal direction of the device body, and the means of the folding back section functions in the distal or a proximal direction of the device body.

The insertion device according to the present invention comprises, for example, an endoscope or catheter for medical or industrial use, a device used through a forceps hole of an endoscope, a device for maintenance of dilapidated buildings or examination of the inside of buildings upon disaster rescue, by insertion into an opening, and the like. Especially, the insertion device according to the present invention is suitably used in an endoscopic surgery such as a laparoscopic surgery. When the insertion device according to the present invention is used in an endoscopic surgery and the like, the folding back sections disposed in the serially located positions by the operation means are inserted into the body through an incision in the body surface, from the folding back section at the distal portion of the device body. At that time, disposed in the serially located positions, the folding back sections can be inserted into the body through a small incision while keeping the external diameter small.

After the folding back sections and the distal section of the device body are inserted, the folding back sections are moved to the folded back positions by the operation means in a cavity in the body. In this way, it becomes possible to have the means of the device body function in the distal direction of the device body, and the means of the folding back sections function in the distal or proximal direction of the device body. As described above, the insertion device according to the present invention has a plurality of functions, among various means such as an observation means, a diagnosis means and a treatment means, and can perform a diversity of examinations, treatments and the like by itself.

After the treatment and the like is finished, the folding back sections are again moved to the serially located positions again by the operation means, and pulled out of the body through the incision. At that time, disposed in the serially located positions, the folding back sections can be pulled out of the body through the small incision while keeping the external diameter small.

As described above, the insertion device according to the present invention has excellent insertability and removability in that the insertion device can be readily inserted and extracted through a small incision while keeping the external diameter small and no larger than the external diameter of the device body. Also, compared with a laparotomy surgery or the use of conventional multifunctional endoscopes, the incision can be made smaller, thus reducing physical and mental burden of the patient. In the case of industrial use, insertion and extraction are readily performed through a small insertion opening. The insertion device according to the present invention can be multifunctionalized without harming the excellent insertability, and can also be highly-functionalized as a result of the multifunctionalization. Also, it is possible to select, in accordance with the intended use, one where the means of the folding back section functions in the distal direction of the device body, or one where the means of the folding back section functions in the proximal direction, thus extending the range of application.

Means mounted on the device body and the folding back sections comprise various means that have functions including an observation function, a diagnosis function and a treatment function, such as a CCD camera, forceps, a snare, various microsensors, an actuator, a lighting, an ultrasound irradiation device, and a dosing device, for example. Among those means, the device body and the folding back sections may have the same or different means, and each of the device body and the folding back sections may have one or a plurality of those means. In such a case, the insertion device according to the present invention can constitute an endoscope for medical or industrial use, or a device that is used through a catheter or a forceps hole of an endoscope.

The operation means can have any configuration as long as the folding back section can be moved to a serially located position and a folded back position. The operation means comprises, for example: a configuration in which the folding back section is moved to the folded back position by pulling a wire rod, formed from superelastic alloy wire, etc., attached to the folding back section from the outside, and the folding back section is moved back to the serially located position by pulling a wire rod attached to the folding back section from the inside; or a configuration in which the folding back section is driven, relative to the device body, to move to the serially located position and the folded back position, by means of expansion and contraction actions of a shape-memory alloy or an activation mechanism, such as a hydraulically-activated actuator or piezoelectric actuator, attached to the connecting section of the folding back section and the device body.

In the insertion device according to the present invention, preferably, a plurality of the folding back sections are provided, each folding back section having at least one of the various means and being provided to be aligned in the longitudinal direction of the device body in such a manner that each folding back section can be folded back relative to an adjacent folding back section on the proximal side of the device body or to the device body; the operation means is provided in such a manner that the operation means can move each folding back section to a serially located position in which each folding back section is aligned with an adjacent folding back section on the proximal side of the device body or with the device body, and to a folded back position in which each folding back section is folded back relative to an adjacent folding back section on the proximal side of the device body or to the device body; and when each folding back section is moved to the folded back position by the operation means, the means of the device body functions in the distal direction of the device body, and the means of each folding back section functions in the distal or proximal direction of the device body. Even in such a case, insertion and extraction of the insertion device can be readily performed through a small incision or insertion opening while keeping the external diameter small and no larger than that of the device body, thus allowing for excellent insertability. Also, many more means can be mounted, allowing a single insertion device to perform more examinations, treatment, and the like. Consequently, further multifunctionalzation and high-functionalization can be achieved. By preparing ones where the direction in which means of each folding back section functions is freely modified, the range of application can be further expanded.

In the insertion device according to the present invention, among the folding back sections, two of the folding back sections may have an image obtaining means. In such a case, stereoscopic viewing can be performed by the two image obtaining means. Consequently, information on the breadth and depth of visual field as visual information, which has often been lacking with an insertion device such as conventional monocular endoscopes, can be obtained, making it possible to perform detailed, highly precise and safe examinations, treatment and the like. The image obtaining means is preferably able to obtain a moving image, and comprises a CCD camera, for example.

In the insertion device according to the present invention, each folding back section may comprise a first folding back section disposed at the very tip and a second folding back section disposed between the first folding back section and the device body; and the operation means may be configured to include a first wire rod having one end fixed to the tip portion of the lateral surface of the first folding back section, a second wire rod having one end fixed to the lateral surface of the first folding back section or the second folding back section, and a third wire rod passing inside the first folding back section, the second folding back section and the device body and having one end fixed to the inside of the first folding back section; and configured to move the first folding back section to the folded back position by pulling the first wire rod to the proximal direction of the device body; move the second folding back section to the folded back position by pulling the second wire rod to the proximal direction of the device body; and move the first folding back section and the second folding back section to the serially located positions by pulling the third wire rod to the proximal direction of the device body. In such a case, at least three means can be mounted on the device body, the first folding back section and the second folding back section. Also, by operating the first wire rod, the second wire rod and the third wire rod, the first folding back section and the second folding back section can be readily moved to each of the serially located position and the folded back position. The first wire rod, the second wire rod and the third wire rod are preferably biocompatible.

In the insertion device according to the present invention, the tip portion of the device body may be configured to be bendable. In such a case, it is possible to have means of the device body and means of each folding back section function not only in the distal and proximal directions of the device body but also in various directions.

A feature of the endoscope according to the present invention is in that the insertion device according to the present invention is attached to a forceps hole. In the endoscope according to the present invention, a plurality of functions of the insertion device can be added in addition to the functions already equipped, and therefore, further multifunctionalization and high-functionalization are achieved.

Advantageous Effects of Invention

According to the present invention, an insertion device and an endoscope which are readily inserted and extracted through a small incision and have multiple functions are provided.

BRIEF DESCRIPTION OF DRAWINGS

FIG. 3 illustrates a usage state of the insertion device of FIG. 1 in a laparoscopic surgery, wherein FIG. 3(a) is a partially-sectioned side view; FIG. 3(b) is an enlarged perspective view illustrating when the insertion device is inserted into the body; and FIG. 3(c) is an enlarged perspective view of the insertion device upon treatment.

DESCRIPTION OF EMBODIMENTS

Figure 1:
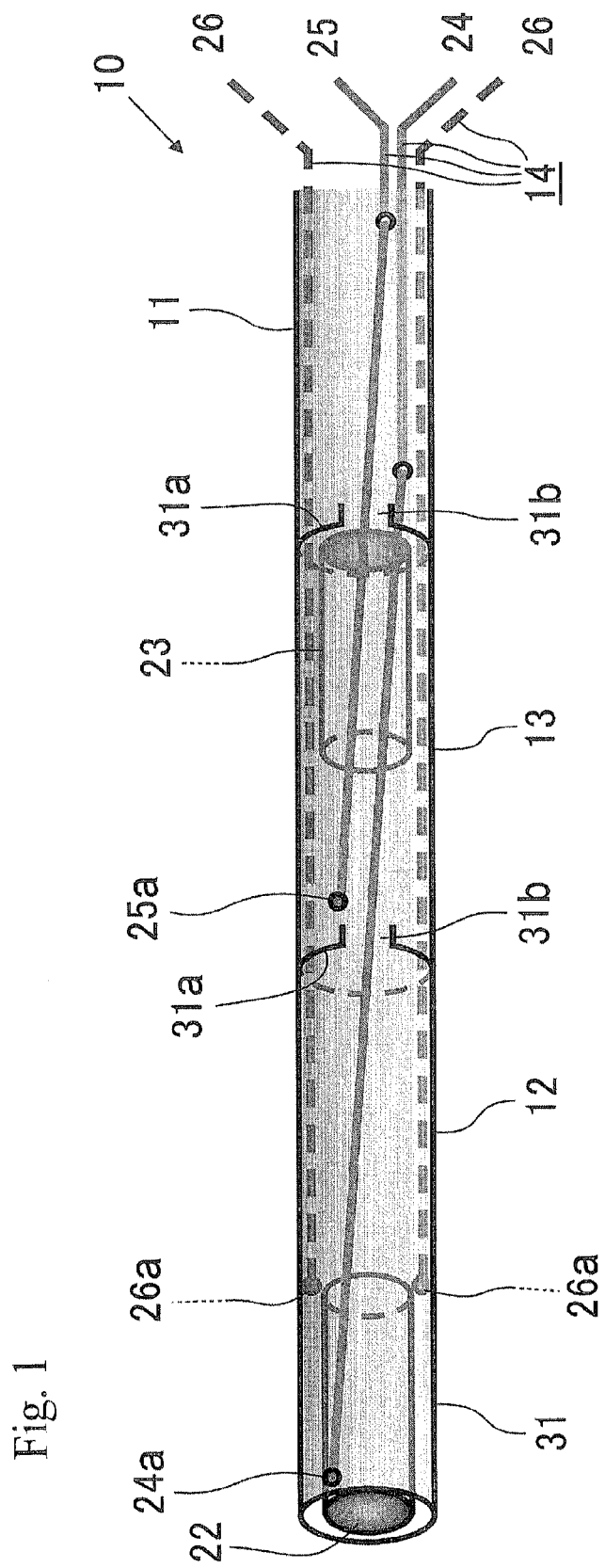
FIG. 1 is a perspective view illustrating an insertion device of a first embodiment of the present invention.
Figure 2:
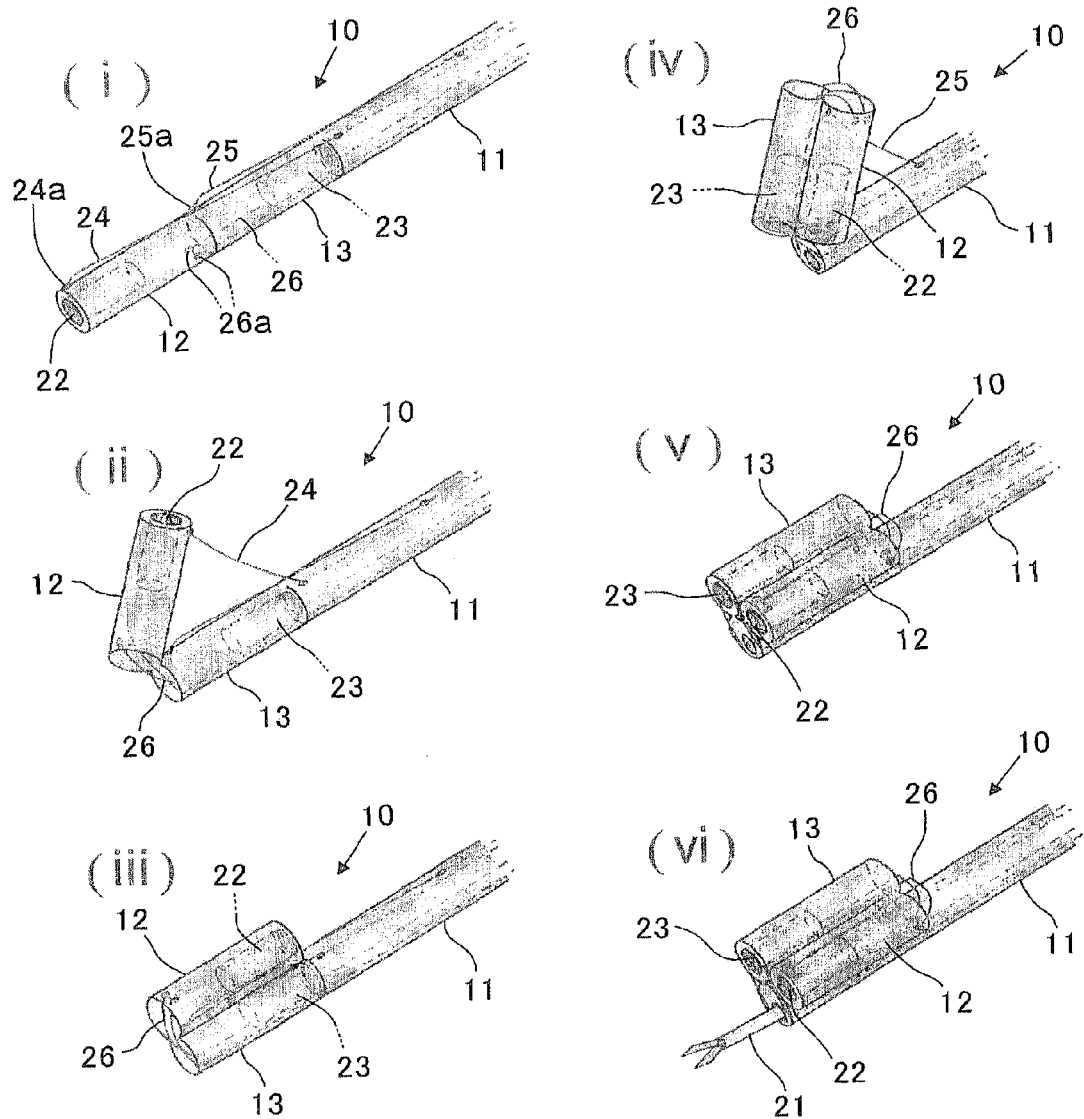
FIG. 2 is a perspective view illustrating the transformed state of the insertion device of FIG. 1, from a serially located position to a folded back position.
Figure 3:
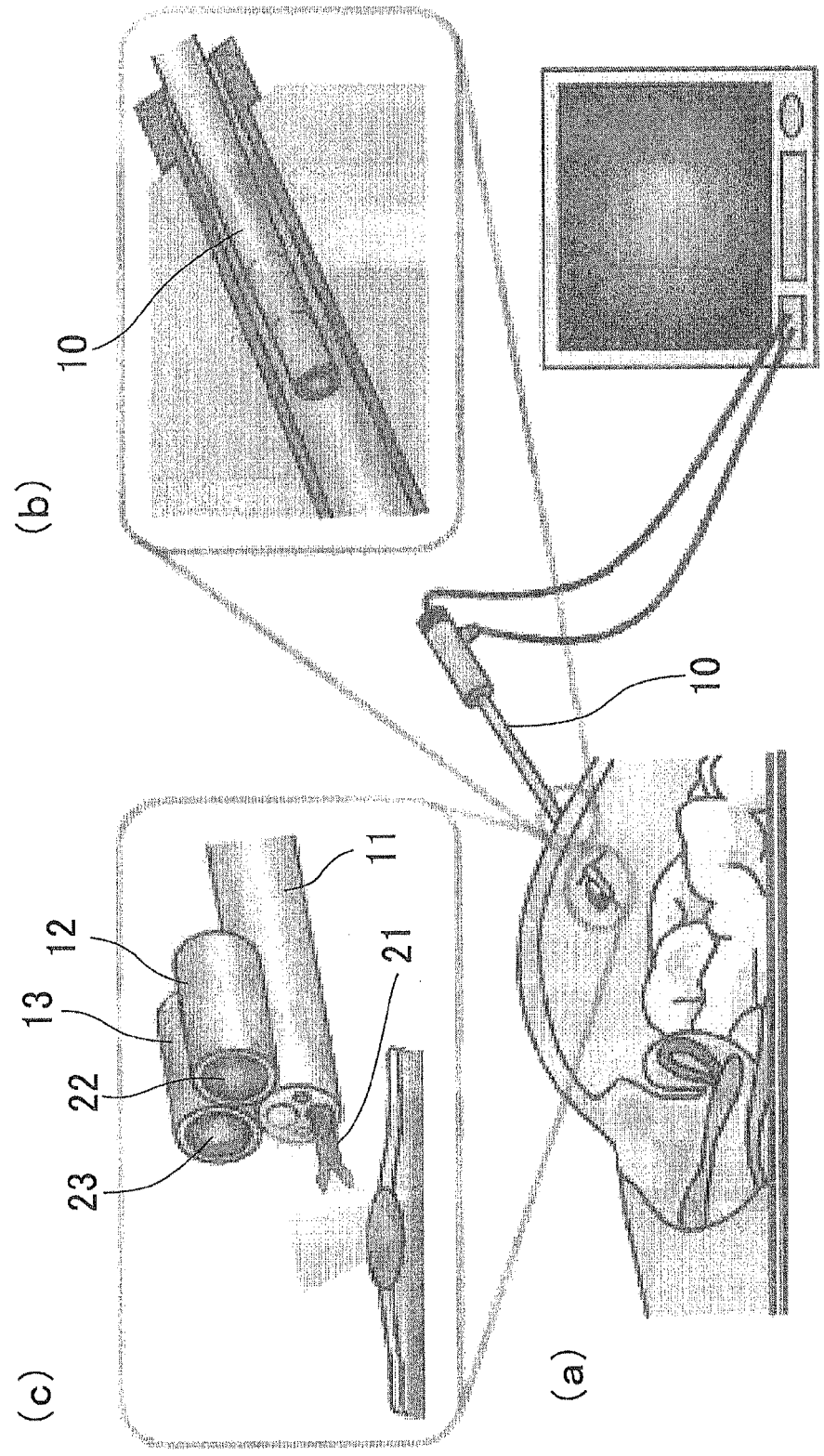

Now, embodiments of the present invention will be explained with reference to the drawings. FIGS. 1 to 3 illustrate an insertion device of a first embodiment of the present invention. As shown in FIGS. 1 to 3, an insertion device 10 of the first embodiment of the present invention comprises an endoscope, and has a device body 11, a first folding back section 12, a second folding back section 13, and an operation means 14.

As shown in FIGS. 1 to 3, the device body 11 is elongated and has a grip forceps 21 as a treatment means. The grip forceps 21 is adapted to extend and function in the distal direction of the device body 11.

The first folding back section 12 and the second folding back section 13 are elongated and provided at the distal portion of the device body 11 in such a manner that the first and second folding back sections are aligned in a row in the longitudinal direction of the device body 11. The first folding back section 12 is disposed at the very tip of the device body 11 and has an image obtaining means 22. The second folding back section 13 is disposed between the first folding back section 12 and the device body 11 and has an image obtaining means 23. The image obtaining means 22, 23 respectively comprise a lighting and a CCD camera (a multipurpose camera manufactured by RF Co., Ltd.) that is capable of obtaining a moving image, as an observation means.

As shown in FIG. 1, the outer walls of the device body 11, the first folding back section 12 and the second folding back section 13 are covered by a tube 31 which is made from an elongated thin silicone rubber, and integrally formed with each other. In the tube 31, slits 31a are formed at the boundary between the device body 11 and the second folding back section 13, and at the boundary between the second folding back section 13 and the first folding back section 12. In this way, the device body 11 and the second folding back section 13, and the second folding back section 13 and the first folding back section 12 are connected only by parts 31b of the tube 31. As the part 31b of the tube 31 functions as a joint, the first folding back section 12 can be folded back relative to the adjacent second folding back section 13, to the proximal side of the device body 11. Also, as the part 31b of the tube 31 functions as a joint, the second folding back section 13 can be folded back relative to the adjacent device body 11, to the proximal side of the device body 11. The first folding back section 12 and the second folding back section 13 can be folded back by being rotated around an axis perpendicular to the longitudinal direction of the device body 11. In each of the device body 11, the first folding back section 12 and the second folding back section 13, the grip forceps 21, the image obtaining means 22 and the image obtaining means 23 are respectively housed in the tube 31.

As shown in FIGS. 1 and 2, the operation means 14 has a first wire rod 24, a second wire rod 25, and two third wire rods 26 that are formed from biocompatible, superelastic alloy wire. One end 24a of the first wire rod 24 is fixed to the tube 31 at the tip portion of the lateral surface of the first folding back section 12. The first wire rod 24 passes outside the tube 31 from the one end 24a fixed to the tube 31, penetrates the tube 31 at the distal section of the device body 11 and enters the tube 31, and extends to the proximal portion of the device body 11. The second wire rod 25 is fixed to the tube 31 at the tip portion of the lateral surface of the second folding back section 13. The second wire rod 25 passes outside the tube 31 from one end 25a fixed to the tube 31, penetrates the tube 31 at a position on the proximal side, with respect to the first wire rod 24, of the device body 11 and enters the tube 31, and extends to the proximal portion of the device body 11.

One end 26a of each of the third wire rods 26 is fixed to the internal surface of the tube 31 between the central portion and the rear-end portion of the first folding back section 12. Each of the third wire rods 26 passes inside the tube 31 of the first folding back section 12, the second folding back section 13 and the device body 11, from the one end 26a fixed to the tube 31, and extends to the proximal portion of the device body 11.

As shown in FIG. 2(i) to (iii), the operation means 14 can move the first folding back section 12 to a folded back position in which the first folding back section 12 is folded back relative to the second folding back section 13, by pulling the first wire rod 24 in the proximal direction of the device body 11. Also, as shown in FIG. 2(iv) to (v), the operation means 14 can move the second folding back section 13 to a folded back position in which the second folding back section 13 is folded back relative to the device body 11, by pulling the second wire rod 25 in the proximal direction of the device body 11. Furthermore, the operation means 14 can move the first folding back section 12 and the second folding back section 13 to serially located positions in which the first and second folding back sections are aligned in a row with the device body 11, by pushing the first wire rod 24 and the second wire rod 25, pulled to the proximal side of the device body 11, to the distal side of the device body 11 by the amount the first and second wire rods were pulled, and by pulling the third wire rods 26 in the proximal direction of the device body 11. As described above, the operation means 14 can move the first folding back section 12 and the second folding back section 13 to the serially located positions and the folded back positions.

As shown in FIGS. 2(vi) and 3, the insertion device 10 is configured such that, when the first folding back section 12 and the second folding back section 13 are moved to the folded back positions by the operation means 14, the grip forceps 21 of the device body 11, the image obtaining means 22 of the first folding back section 12 and the image obtaining means 23 of the second folding back section 13 function in the distal direction of the device body 11.

It should be noted that in a specific example, the device body 11, the first folding back section 12 and the second folding back section 13 have an external diameter of about 10 mm, and the insertion device 10 has a length of about 130 mm with the device body 11, the first folding back section 12 and the second folding back section 13 aligned in a row. Each of the first folding back section 12 and the second folding back section 13 has a length of 40 mm, and the CCD camera of each of the image obtaining means 22, 23 has a diameter of 5.5 mm and a length of 20 mm. Also, inside the tube 31, not only each of the image obtaining means 22, 23 or the grip forceps 21, but also a thin polyimide tube for passing, inside, wirings of the CCD camera, the first wire rod 24, the second wire rod 25 and each of the third wire rods 26, and a polymer tube that secures the forceps hole and the like are housed.

Now, the actions will be explained. As shown in FIG. 3, the insertion device 10 is suitably used in an endoscopic surgery such as a laparoscopic surgery. When used in an endoscopic surgery and the like, as shown in FIG. 3 (b), the first folding back section 12 and the second folding back section 13 disposed in the serially located positions by the operation means 14 are inserted into the body through an incision in the body surface, from the first folding back section 12 at the tip. At that time, disposed in the serially located positions, the first folding back section 12 and the second folding back section 13 can be inserted into the body through a small incision while keeping the external diameter small.

After the first folding back section 12, the second folding back section 13, and the distal section of the device body 11 are inserted, as shown in FIG. 3(a), the first folding back section 12 and the second folding back section 13 are moved to the folded back positions by the operation means 14 in a cavity in the body. In this way, as shown in FIG. 3(c), it becomes possible for the grip forceps 21 of the device body 11 and each of the image obtaining means 22, 23 of the first folding back section 12 and the second folding back section 13 to function in the distal direction of the device body 11. At that time, a three-dimensional image is obtained by the two image obtaining means 22, 23, and therefore, information on the breadth and depth of visual field as visual information, which has often been lacking with conventional monocular endoscopes, can be obtained, making it possible to perform detailed and highly precise examinations, treatment and the like.

As described above, when inserting the insertion device 10 into the body, for example, usual two-dimensional visual information from the image obtaining means 22 of the first folding back section 12 is used, and at a location where delicate operations are required, such as an area that is treated, stereoscopic visual information from each of the image obtaining means 22, 23 of the first folding back section 12 and the second folding back section 13 can be used.

After the treatment and the like is finished, the first folding back section 12 and the second folding back section 13 are moved to the serially located positions again by the operation means 14, and pulled out of the body through the incision. At that time, disposed in the serially located positions, the first folding back section 12 and the second folding back section 13 can be pulled out of the body through the small incision while keeping the external diameter small.

The insertion device 10 has excellent insertability and removability in that the insertion device 10 can be readily inserted and extracted through a small incision while keeping the external diameter small and no larger than the external diameter of the device body 11. Also, compared with a laparotomy surgery or the use of conventional multifunctional endoscopes, the incision can be made smaller, thus reducing physical and mental burden of the patient.

In a conventional stereoscopic endoscope, two CCD cameras are implemented and aligned in the direction of the short axis of the stereoscopic endoscope, and therefore, either the size or the observation performance of the stereoscopic endoscope was needed to be sacrificed. On the other hand, the observation performance of the insertion device 10 can be enhanced without harming its excellent insertability, allowing for multifunctionalization and high-functionalization.

It should be noted that means mounted on the device body 11, the first folding back section 12 and the second folding back section 13 are not limited to the grip forceps 21 or the image obtaining means 22, 23, and may comprise any of various means that have functions including an observation function, a diagnosis function and a treatment function, such as a snare, various microsensors, an actuator, an ultrasound irradiation device, and a dosing device, for example. Also, among those means, the device body 11, the first folding back section 12 and the second folding back section 13 may have the same or different means, and each of the device body 11, the first folding back section 12 and the second folding back section 13 may have one or a plurality of those means. In such a case, the insertion device 10 can constitute not only an endoscope but also a device that is used through a catheter or a forceps hole of an endoscope, and can be configured to perform a diversity of examinations, treatments and the like by itself.

Also, the number of the folding back sections is not limited to two, and may be three or more. In such a case, a greater number of means can be mounted, and more examinations, treatments and the like can be performed by a single insertion device 10. Consequently, further multifunctionalization and high-functionalization can be achieved.

The operation means 14 may have a configuration to activate the first folding back section 12 and the second folding back section 13 by an activation mechanism such as an actuator. Also, the insertion device 10 may be adapted to be able to insert a rigid stylet into the tube 31 so that the first folding back section 12 and the second folding back section 13 will not bend when inserted into the body.

It should be noted that since the size of the insertion device 10 can be made smaller, in the future, by using an imager smaller than a CCD camera of $\phi 5.5$ mm as the image obtaining means 22, 23, it is expected to be able to provide three-dimensional visual-field information at various locations in the body. Also, by further miniaturizing/high-functionalizing various means or the operation means 14 mounted on the device body 11, the first folding back section 12, the second folding back section 13, etc. by means of MEMS (microelectromechanical systems) technology and the like, it is expected, in the future, to be able to provide means for various, highly-flexible examinations/treatments in various areas, in addition to an abdominal cavity, such as an eyeball, bladder, heart, uterus holding a fetus therein, brain ventricle, chest cavity, nasal cavity, while securing the insertability with a small incision.

It should be noted that as the insertion device 10, ones where the direction in which means of the first folding back section 12 and the second folding back section 13 function is freely changed in the distal or proximal direction of the device body 11 may be prepared. In such a case, the range of application can be extended by using it in accordance with the intended use.

Figure 4:
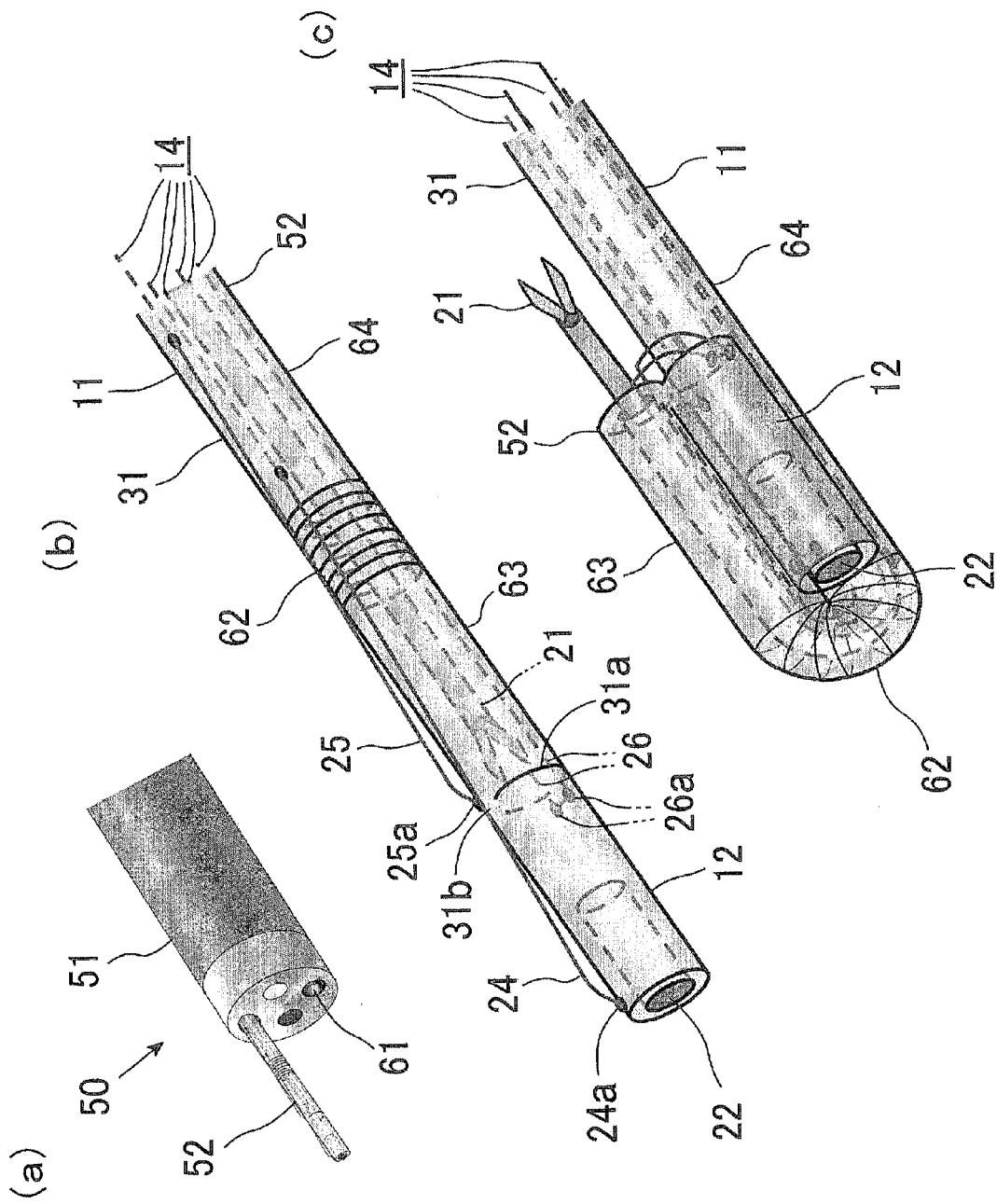
FIG. 4(a) is a perspective view illustrating an endoscope of an embodiment of the present invention.
FIG. 4(b) is a perspective view illustrating an insertion device of a second embodiment of the present invention.
FIG. 4(c) is a perspective view illustrating the transformed state of the insertion device of the second embodiment of the present invention.
Figure 5:
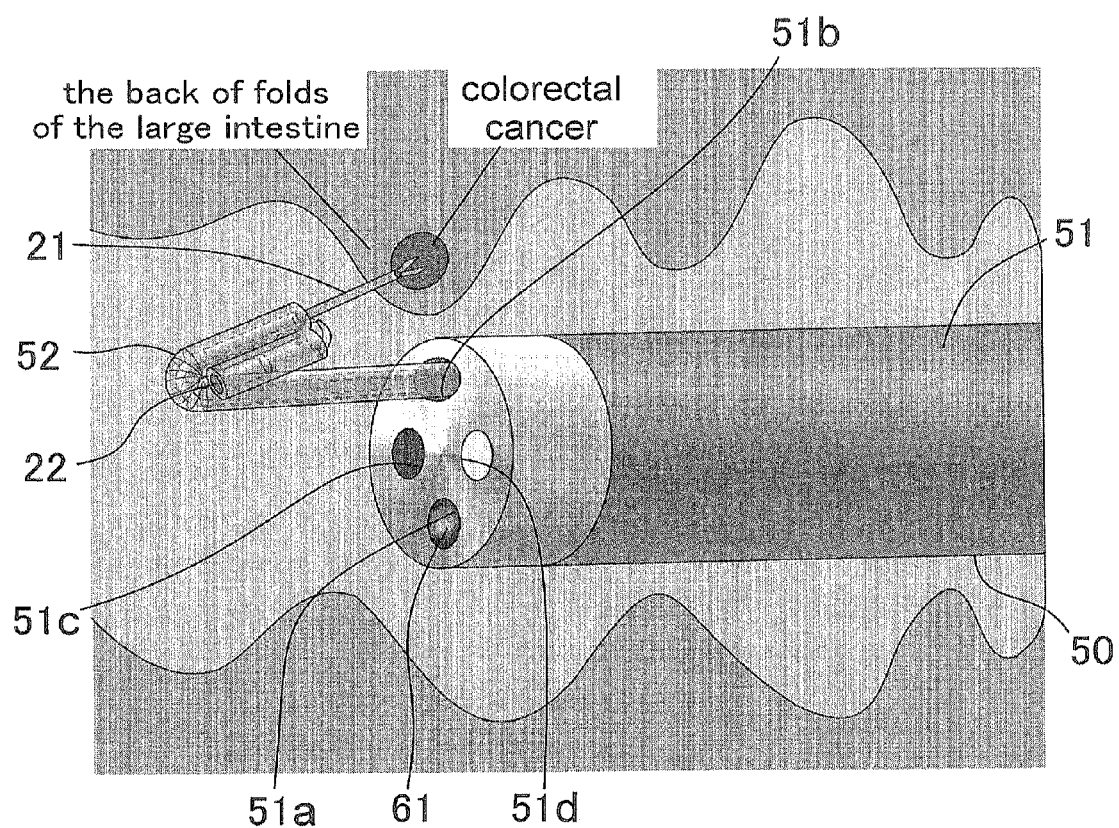
FIG. 5 is a perspective view illustrating the usage state of the endoscope of FIG. 4(a) in the large intestine.

FIGS. 4 and 5 illustrate an endoscope of an embodiment of the present invention and an insertion device of a second embodiment of the present invention. As shown in FIGS. 4 and 5, an endoscope 50 of the embodiment of the present invention has an endoscope body 51 and an insertion device 52. It should be noted that the insertion device 52 has almost the same configurations as those of the insertion device 10 of the first embodiment of the present invention. Therefore, in the following explanations, the configurations same as those of the first embodiment of the present invention are denoted by the same reference characters, and overlapping explanations on their actions/effects are omitted.

The endoscope body 51 comprises a commercially-available endoscope and has four forceps holes 51a, 51b, 51c, 51d at the tip. The endoscope body 51 has, in the forceps hole 51a, an image obtaining means 61 comprising a lighting and a CCD camera that can obtain a moving image. In the endoscope body 51, the insertion device 52 is inserted in the forceps hole 51b. Also, in the endoscope body 51, the other forceps holes 51c, 51d are equipped with any of various means such as an observation means, a diagnosis means and a treatment means.

The insertion device 52 comprises a small endoscope and is extendably and retractably inserted into the forceps hole 51b of the endoscope body 51. The insertion device 52 has the device body 11, the first folding back section 12 and the operation means 14. The device body 11 is elongated and has the grip forceps 21 as a treatment means. The grip forceps 21 is adapted to extend and function in the distal direction of the device body 11. The device body 11 has a bending section 62 at a predefined distance from the tip, and can be bent at the bending section 62. In the device body 11, a distal section 63 on the distal side with respect to the bending section 62 can be bent at a given angle between a position in which the distal section 63 is extended straight relative to a proximal section 64 on the proximal side with respect to the bending section 62 and a position in which the distal section 63 is bent 180 degrees.

The first folding back section 12 is elongated and provided at the distal portion of the device body 11 in such a manner that the first folding back section 12 is aligned in a row in the longitudinal direction of the device body 11. The first folding back section 12 has the image obtaining means 22 comprising a lighting and a CCD camera that can obtain a moving image, as an observation means.

As shown in FIG. 4, the outer walls of the device body 11 and the first folding back section 12 are covered by a tube 31 which is made from an elongated thin silicone rubber, and are integrally formed with each other. In the tube 31, a slit 31a is formed at the boundary between the device body 11 and the first folding back section 12. In this way, the device body 11 and the first folding back section 12 are connected only by the part 31b of the tube 31. As the part 31b of the tube 31 functions as a joint, the first folding back section 12 can be folded back relative to the device body 11, toward the proximal side of the device body 11. The first folding back section 12 can be folded back by being rotated around an axis perpendicular to the longitudinal direction of the device body 11. In the device body 11 and the first folding back section 12, the grip forceps 21 and the image obtaining means 22 are respectively housed in the tube 31.

The operation means 14 has the first wire rod 24, the second wire rod 25, and the two third wire rods 26 that are formed from biocompatible, superelastic alloy wire. The one end 24a of the first wire rod 24 is fixed to the tube 31 at the tip portion of the lateral surface of the first folding back section 12. The first wire rod 24 passes outside the tube 31 from the one end 24a fixed to the tube 31, penetrates the tube 31 at the proximal section 64 of the device body 11 and enters the tube 31, and extends to the proximal portion of the device body 11. The second wire rod 25 is fixed to the tube 31 at the tip portion of the lateral surface of the distal section 63 of the device body 11. The second wire rod 25 passes outside the tube 31 from the one end 25a fixed to the tube 31, penetrates the tube 31 at a position on the proximal side, with respect to the first wire rod 24, of the device body 11 and enters the tube 31, and extends to the proximal portion of the device body 11. The one end 26a of each of the third wire rods 26 is fixed to the internal surface of the tube 31 at the rear-end portion of the first folding back section 12. Each of the third wire rods 26 passes inside the tube 31 of the first folding back section 12 and the device body 11, from the one end 26a fixed to the tube 31, and extends to the proximal portion of the device body 11.

The operation means 14 can move the first folding back section 12 to a folded back position in which the first folding back section 12 is folded back relative to the device body 11, by pulling the first wire rod 24 in the proximal direction of the device body 11. Also, the operation means 14 can bend the distal section 63 of the device body 11 at a given angle relative to the proximal section 64, by pulling the second wire rod 25 in the proximal direction of the device body 11. Furthermore, the operation means 14 can move the first folding back section 12 and the distal section 63 of the device body 11 to serially located positions in which the first folding back section 12 and the distal section 63 of the device body 11 are aligned in a row with the proximal section 64 of the device body 11, by pushing the first wire rod 24 and the second wire rod 25, pulled to the proximal side of the device body 11, to the distal side of the device body 11 by the amount the first and second wire rods were pulled, and by pulling the third wire rods 26 in the proximal direction of the device body 11.

As shown in FIGS. 4 and 5, the insertion device 52 is configured such that, when the first folding back section 12 is moved to the folded back position by the operation means 14, the grip forceps 21 of the device body 11 and the image obtaining means 22 of the first folding back section 12 function in the distal direction of the distal section 63 of the device body 11.

It should be noted that in a specific example, in the insertion device 52, the device body 11 and the first folding back section 12 have an external diameter of about 3 mm. The first folding back section 12 and the distal section 63 of the device body 11 have a length of 10 mm. Also, inside the tube 31, not only the image obtaining means 22 or the grip forceps 21, but also a thin polyimide tube for passing, inside, wirings of the CCD camera, the first wire rod 24, the second wire rod 25 and each of the third wire rods 26, and a polymer tube that secures the forceps hole and the like are housed. The endoscope body 51 has an external diameter of 11 to 13 mm, and each of the forceps holes 51a, 51b, 51c, 51d has an internal diameter of 3.2 mm.

Now, the actions will be explained. In the endoscope 50, the insertion device 52 is attached to the forceps hole 51b, and therefore, in addition to the functions already equipped in the endoscope body 51, a plurality of functions of the insertion device 52 can be added, and further multifunctionalization and high-functionalization can be achieved. Since the tip portion of the device body 11 of the insertion device 52 is configured to be bendable at the bending section 62, it is possible to have the grip forceps 21 of the device body 11 and the image obtaining means 22 of the first folding back section 12 function not only in the distal and proximal directions of the device body 11 but also in various directions. Therefore, as shown in FIG. 5, it is possible to use the endoscope 50 for an area that does not face the insertion direction of the endoscope 50, such as the back of folds of the large intestine. Also, for an area that faces the insertion direction of the endoscope 50, a three-dimensional image can be obtained by means of the image obtaining means 22 of the first folding back section 12 and the image obtaining means 22 of the endoscope body 51.

It should be noted that the insertion device 10 and endoscope 50 may be used not only as a minimally invasive medical device but also for industrial use. Even in such a case, insertion and extraction through a small insertion hole as well as other various functions are possible. Examples of the industrial use are corrosion survey or repair work for rust in the plumbing, etc., inspection or repair work of the inside of a machine such as a jet engine, nuclear container, or power-generating turbine, and maintenance of dilapidated buildings or work performed upon disaster rescue, to examine the inside of buildings, by insertion into an opening too small for people to go in.

REFERENCE SIGNS LIST

10 Insertion Device
11 Device Body
12 First Folding Back Section
13 Second Folding Back Section
14 Operation Means
21 Grip Forceps
22, 23 Image Obtaining Means
24 First Wire Rod
25 Second Wire Rod
27 Third Wire Rod
31 Tube

The invention claimed is:

1. An insertion device comprising:
an elongated device body having at least one of various means including an observation means, a diagnosis means and a treatment means;
a folding back section having at least one of the various means and provided at a distal portion of the device body in such a manner that the folding back section can be folded back to a proximal side of the device body; and
an operation means provided in such a manner that the operation means can move the folding back section to a serially located position in which the folding back section is aligned with the distal portion of the device body and to a folded back position in which the folding back section is folded back to the proximal side of the device body; wherein
when the folding back section is moved to the folded back position by the operation means, the means of the device body functions in a distal direction of the device body, and the means of the folding back section functions in the distal or a proximal direction of the device body, wherein
a plurality of the folding back sections are provided, each folding back section having at least one of the various means and being provided to be aligned in the longitudinal direction of the device body in such a manner that each folding back section can be folded back relative to an adjacent folding back section on the proximal side of the device body or to the device body;
the operation means is provided in such a manner that the operation means can move each folding back section (i) to a serially located position in which each folding back section is aligned with the adjacent folding back section on the proximal side of the device body or with the device body, and (ii) to a folded back position in which each folding back section is folded back relative to the adjacent folding back section on the proximal side of the device body or to the device body;
the device body and each of the folding back sections are aligned in a row in the longitudinal direction of the device body when each of the folding back sections is in the serially located position; and
when each folding back section is moved to the folded back position by the operation means, the means of the device body functions in the distal direction of the device body, and the means of each folding back section functions in the distal or proximal direction of the device body; and
when the plurality of the folding back sections are moved to the folded back position, the plurality of the folding back sections are axially aligned around a circumference of the device body.

2. The insertion device according to claim 1, wherein among the folding back sections, two of the folding back sections have an image obtaining means.

3. The insertion device according to claim 2, wherein
each folding back section comprises a first folding back section disposed at the tip and a second folding back section disposed between the first folding back section and the device body; and
the operation means is configured to include a first wire rod having one end fixed to a tip portion of a lateral surface of the first folding back section, a second wire rod having one end fixed to the lateral surface of the first folding back section or the second folding back section, and a third wire rod passing inside the first folding back section, the second folding back section and the device body and having one end fixed to the inside of the first folding back section; and configured to move the first folding back section to the folded back position by pulling the first wire rod to the proximal direction of the device body; move the second folding back section to the folded back position by pulling the second wire rod to the proximal direction of the device body; and move the first folding back section and the second folding back section to the serially located positions by pulling the third wire rod to the proximal direction of the device body.

4. The insertion device according to claim 3, wherein the tip portion of the device body is configured to be bendable.

5. The insertion device according to claim 2, wherein the tip portion of the device body is configured to be bendable.

6. The insertion device according to claim 1, wherein
each folding back section comprises a first folding back section disposed at the tip and a second folding back section disposed between the first folding back section and the device body; and
the operation means is configured to include a first wire rod having one end fixed to a tip portion of a lateral surface of the first folding back section, a second wire rod having one end fixed to the lateral surface of the first folding back section or the second folding back section, and a third wire rod passing inside the first folding back section, the second folding back section and the device body and having one end fixed to the inside of the first folding back section; and configured to move the first folding back section to the folded back position by pulling the first wire rod to the proximal direction of the device body; move the second folding back section to the folded back position by pulling the second wire rod to the proximal direction of the device body; and move the first folding back section and the second folding back section to the serially located positions by pulling the third wire rod to the proximal direction of the device body.

7. The insertion device according to claim 6, wherein the tip portion of the device body is configured to be bendable.

8. The insertion device according to claim 1, wherein the tip portion of the device body is configured to be bendable.

9. An endoscope, wherein the insertion device according to claim 1 is attached to a forceps hole.

10. An endoscope, wherein the insertion device according to claim 2 is attached to a forceps hole.

11. An endoscope, wherein the insertion device according to claim 6 is attached to a forceps hole.

12. An endoscope, wherein the insertion device according to claim 8 is attached to a forceps hole.

13. An endoscope, wherein the insertion device according to claim 3 is attached to a forceps hole.

14. An endoscope, wherein the insertion device according to claim 5 is attached to a forceps hole.

15. An endoscope, wherein the insertion device according to claim 7 is attached to a forceps hole.

16. An endoscope, wherein the insertion device according to claim 4 is attached to a forceps hole.

* * * * *